United States Patent [19]

Kajihara et al.

[11] Patent Number: 5,621,086
[45] Date of Patent: Apr. 15, 1997

[54] SIALIC ACID DERIVATIVE AND METHOD OF MANUFACTURING IT

[75] Inventors: Yasuhiro Kajihara; Takashi Ebata; Hisashi Kodama, all of Yokohama, Japan

[73] Assignee: Japan Tobacco Inc., Tokyo, Japan

[21] Appl. No.: 530,255

[22] PCT Filed: Mar. 14, 1995

[86] PCT No.: PCT/JP95/00418

§ 371 Date: Aug. 31, 1995

§ 102(e) Date: Aug. 31, 1995

[87] PCT Pub. No.: WO95/25115

PCT Pub. Date: Sep. 21, 1995

[30] Foreign Application Priority Data

Mar. 14, 1994 [JP] Japan .................. 6-042859

[51] Int. Cl.$^6$ .................. C07H 13/00; C07H 15/00; A61K 31/70
[52] U.S. Cl. .................. 536/17.4; 536/28.1; 536/28.4; 536/28.5; 536/28.53; 536/28.54; 536/28.55; 536/28.6; 536/27.1; 536/27.6; 536/27.81; 536/53; 536/55.3; 536/26.1; 536/26.7; 536/26.71; 536/26.72
[58] Field of Search .................. 536/17.4, 28.1, 536/18.5, 28.4, 18.6, 28.5, 28.53, 28.54, 28.55, 28.6, 27.1, 27.6, 27.81, 53, 55.3, 26.1, 26.7, 26.71, 26.72, 26.74; 514/25, 43, 45, 46, 47, 48, 49, 50, 51

[56] References Cited

U.S. PATENT DOCUMENTS 5,374,655  12/1994  Kashem et al. .................. 514/540
5,441,932   8/1995  Kodama et al. .................. 514/8

OTHER PUBLICATIONS

E. Simon et al., J. Am. Chem. Soc., 110:7159–7163 (1988).
T. Martin et al., Tetrahedron Letters, 34, No. 11, 1765–1768 (1993).
S. Makino et al., Tetrahedron Letters, 34, No. 17, 2775–2778 (1993).
Yasuhiro Kajihara et al "Carbohydrate Research" (1994) vol. 264, pp. C1–C5.
"J. American Chemical Society" vol. 114, No. 22, 1992, pp. 8748–8750.

*Primary Examiner*—Gary L. Kunz
*Assistant Examiner*—Kathleen Kahler Fonda
*Attorney, Agent, or Firm*—Birch, Stewart, Kolasch & Birch, LLP

[57] ABSTRACT

The present invention is drawn to methods of manufacturing a sialic acid derivative suitable for industrial production. With a method of the present invention, Tetra-O-acetylsialic acid (4a) and acetylcytidine-5'-O-amidite (5a) are condensed in the presence of an acid catalyst to obtain a phosphite (6a). The phosphite (6a) is oxidized with t-butylhydroperoxide to obtain a phosphate (9a). The phosphate (9a) is deprotected with an alkali to obtain CMP-sialic acid (1a).

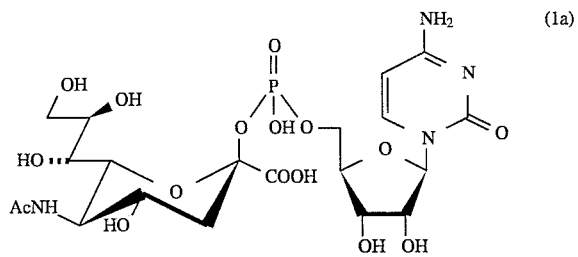

The present invention further encompasses a novel sialic acid derivative.

3 Claims, No Drawings

SIALIC ACID DERIVATIVE AND METHOD OF MANUFACTURING IT

This application is the U.S. national stage of international application PCT/JP 95/00418, filed Mar. 14, 1995.

1. Technical Field

The present invention relates to a method of manufacturing a sialic acid derivative and a novel sialic acid derivative.

2. Prior Art

A sialic acid is a sugar residue binding to ends of various sugar-chain present on a cellular surface layer. Intercellular interaction is mediated with the sialic acid and a substance capable of binding to the sialic acid. For example, it is known that, when an influenza virus invades into a living body, a protein (called hemaglutinine) present on the surface layer of the influenza virus binds to a sialic acid on the surface layer of a erthrocyte, and then the virus invades to the erthrocyte.

To prevent infection with influenza viruses, the following prevention method has been proposed. In the method, a sialic-acid analogue is allowed to bind to a carrier such as a cell or an artificial cell. The carrier is placed in a living body, and viruses are allowed to bind to the sialic acid analogue on the carrier. Therefore, the binding of the viruses to original cells of the living body in vivo, thereby preventing the infection with the viruses. Furthermore, the viruses also may be removed by taking the carrier out of the living body after the viruses bind thereto. At present, a wide variety of therapeutic methods are being studied, using a sialic acid.

Cytidine-5'-monophosphosialic acid (hereinafter referred to as "CMP-sialic acid") represented by the following formula, is known to serve as a sialic-acid donor when a sialic acid transferase (sialyltransferase) acts. The sialic acid transferase transfers the sialic acid from CMP-sialic acid (12) to the sugar chain of a sialic acid acceptor, thereby synthesizing sialoside.

Sialoside described above is known to have various physiological activities. For example, sialoside, known as a ganglioside, having a sialic acid polymer bonded thereto, has a neural growth activity. From the foregoing, it may be understood that the CMP-sialic acid can be used in the synthesis of an anti-virus agent and an anti-dementia agent.

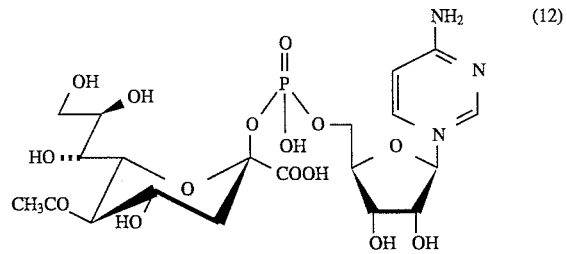

Hence, it is extremely useful to develop a chemical synthetic method for synthesizing a sialic acid derivative represented by CMP-sialic acid in a large amount. Hitherto, the following manufacturing methods of CMP-sialic acid have been reported.

(i) J. Am. Chem. Soc., 110 (1988), 7159–7163;

A sialic acid or a modified sialic acid, namely a sialic acid analogue, is condensed with cytidine-5'-triphosphate using cytidine-5'-monophosphosialic acid synthetase as an enzyme.

(ii) Tetrahedron Lett., 34, 1765, 1993;

After an leaving group is introduced into the 2-position of a sialic acid and a protecting group is introduced into each of hydroxyl groups of the sialic acid, the 2-position of the sialic acid is nucleophilically displaced with a phosphoric acid portion of cytidine-5'-monophosphate and subsequently the protecting group is removed to obtain CMP-sialic acid (12).

(iii) Tetrahedron Lett., 34, 2775, 1993;

After individual hydroxyl groups of cytidine are protected with allyloxycarbamate, allyl N,N,N',N'-tetraisopropylphosphorodiamidite is reacted with the protected cytidine. An allyl N,N-1-diisopropyl phosphoroamidite group is thereby introduced into the 5'-position of cytidine. As a result, a cytidine derivative is obtained. Subsequently, the cytidine derivative is condensed with a sialic acid whose hydroxyl group at the 2-position is protected and whose other hydroxyl groups are protected with allyloxycarbamate, thereby obtaining an intermediate. The phosphoric acid portion of the intermediate is oxidized and the protecting group is removed, thereby obtaining CMP-sialic acid (12).

However, in the aforementioned Method (i), the condensation reaction of some kinds of sialic acid analogues with cytidine-5'-triphosphate mediated by cytidine-5'-monophosialic acid synthetase is not carried out due to the substrate-specificity of the synthetase. In addition, cytidine-5'-monophosphosialic acid synthetase is expensive, resulting in high manufacturing cost. Hence, Method (i) is not suitable for the industrial large-scale production of CMP-sialic acid and the analogues thereof.

The reaction of method (ii) requires completely no-water conditions. Furthermore, it is difficult to purify a product.

In Method (iii), the step of protecting hydroxyl groups with allyloxycarbamate is difficult to perform and the purification of a product is difficult. Since synthesized intermediates in individual steps cannot be isolated, extremely accurate purification of a final product is required. Furthermore, an expensive palladium catalyst is required to remove a protecting group. For these reasons, Method (iii) is not suitable for the industrial large-scale production.

As is described above, any of conventional CMP-sialic acid manufacturing methods is not suitable for the industrial large-scale production. J. Am. Chem., Soc. 114, 8749(1992)(p.8748–8750) discloses that a sialic acid, which has a 2-cyanoethyl N,N-diisopropylphospho amidite group introduced into the 2-position thereof and hydroxyl groups each of which is protected with an acetyl group, is condensed with cytidine whose hydroxyl groups other than that at the 5-position are protected with a benzoyl group, to obtain a condensed compound. However, this document does not disclose that the condensed compound obtained is further deprotected to obtain the desired CMP-sialic acid (12).

DISCLOSURE OF INVENTION

The present invention has been made in view of the above-mentioned problems. The object of the present invention is to provide a suitable method of manufacturing a sialic acid derivative for industrial production and to provide a novel sialic acid derivative. More specifically, the present invention provides a method of manufacturing a sialic acid derivative (1) represented by the following formula:

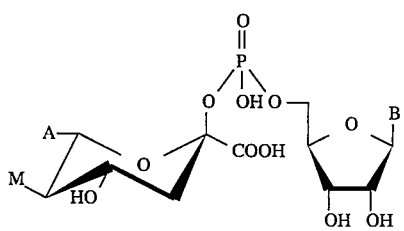

wherein

M is a hydroxyl group or an acetamide group, and

A is a group represented by a formula (2) or (3):

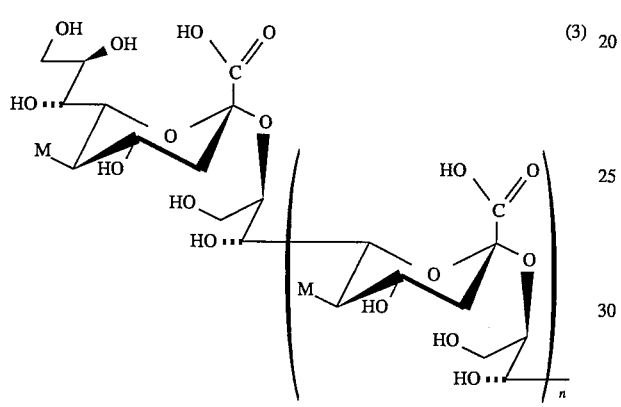

wherein n is an integer of 0, 1 or more, M is the same as defined above, and B is a substituted or unsubstituted nucleic acid base, comprising:

a step of performing a condensation between a compound (4) and a compound (5) represented by the following formulas in the presence of an acid catalyst, thereby obtaining a phosphite derivative (6) represented by the following formula,

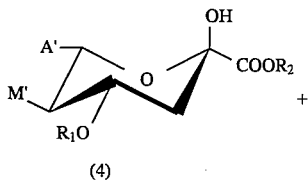

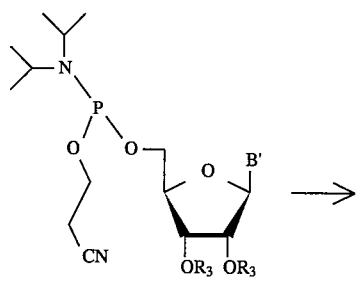

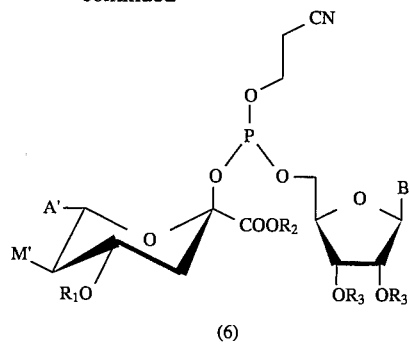

wherein M' indicates —$OR_1$ or an acetamide group, $R_1$ and $R_3$ are an acyl group or a silyl group and may be the same or different to each other, $R_2$ is an alkyl group, and A' indicates a group represented by a formula (7) or (8) shown below:

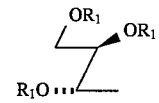

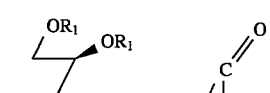

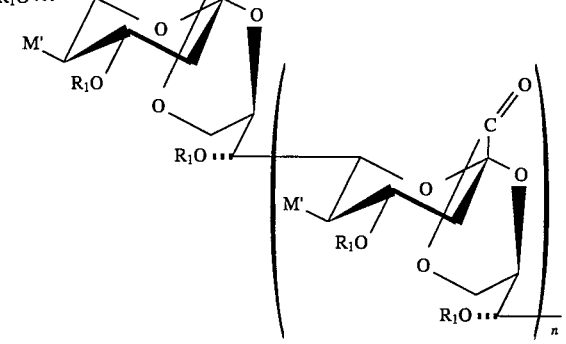

wherein n is an integer of 0, 1 or more, $R_1$ and M' are the same as defined above, and B' is a nucleic acid base whose amino group is protected by an acyl group or a silyl group;

a step of oxidizing a phosphite derivative (6) with an oxidizing agent, thereby obtaining a phosphate derivative (9) represented by the following formula,

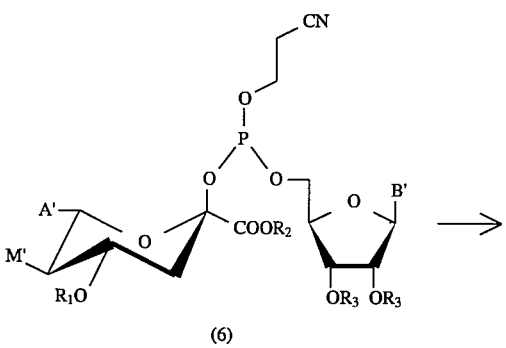

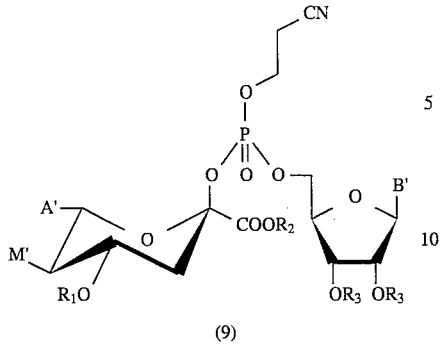

(9)

wherein M', A', B' and $R_1$ to $R_3$ are the same as defined above; and a step of deprotecting said phosphate derivative (9) with an alkali, thereby obtaining said sialic acid derivative (1),

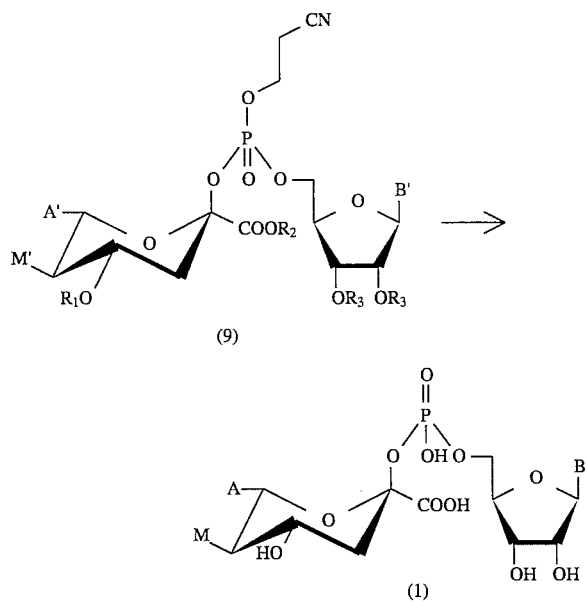

wherein M', M, A, A', B, B' and $R_1$ to $R_3$ are the same as defined above.

In accordance with the aforementioned method, the present inventors have succeeded in obtaining a novel sialic acid derivative (10) represented by the following formula:

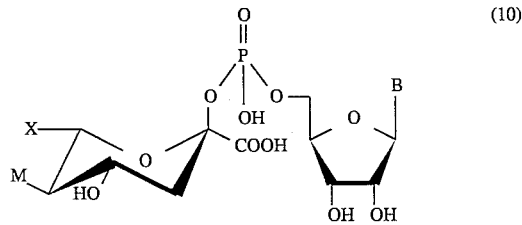

wherein M is a hydroxyl group or an acetamide group, and X is a group represented by a general formula (11):

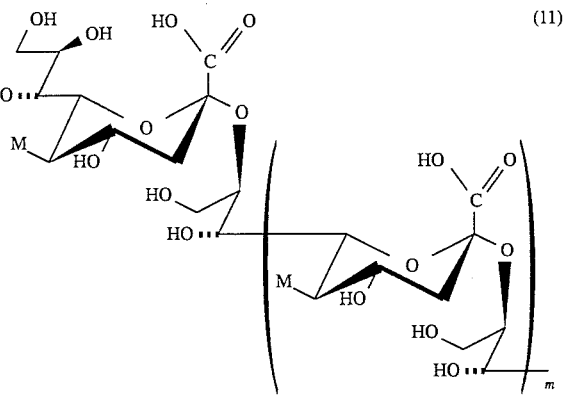

wherein m is an integer of 0 to 3, M is the same defined above, and B is a substituted or unsubstituted nucleic acid base.

Hereinbelow, the present invention will be described in detail.

In the method for manufacturing the sialic acid of the present invention, the compound (4) used as a first starting material is a sialic acid analogue whose hydroxyl groups other than that at the 2-position are individually protected with protecting group $R_1$. Simultaneously, a carboxy group at the 1-position is protected with protecting group $R_2$.

The sialic acid analogue used herein is a sialic acid monomer represented by a general formula (4) in which A' is represented by a general formula (7) or a sialic acid polymer represented by a general formula (4) in which A' is represented by a general formula (8).

As the protecting group $R_1$ or a hydroxyl group, a protecting group capable of being removed by an alkali treatment. More specifically, the protecting group $R_1$ include a substituted or unsubstituted acyl group such as acetyl, monochloroacetyl, benzoyl or pivaloyl, and a silyl ($SiR_3$) group such as trimethylsilyl, t-butyldimethylsilyl, t-butyldiphenylsilyl or triethylsilyl.

The protecting group $R_2$ of a carboxyl group can be removed by an alkali treatment as the same manner as in the case of the protecting group $R_1$. Examples of the protecting group $R_2$ include an alkyl group such as methyl, ethyl or butyl.

Protecting groups $R_1$ and $R_2$ can be introduced into a hydroxyl group and a carboxyl group by a known method.

A commercially-available sialic acid monomer and sialic acid polymer can be used herein. A protecting group is introduced into the sialic acid monomer and sialic acid polymer in accordance with a method of Hasegawa et al. (Hasegawa; Ishida, H.; Kiso, M. J. Carbohydrate Chem. 1993, 12(3), 371–376), thereby obtaining sialic acid analogues. When a protecting group is introduced into the sialic acid polymer, an intramolecular lactone ring is formed. The lactone is opened again in an alkali treatment step described later.

On the other hand, the compound (5) used as a second starting material is a ribonucleic acid derivative. The ribonucleic acid derivative has a 2-cyanoethyl N,N-diisopropyl phosphoroamidite group introduced in the 5-position thereof. N,N-diisopropylphosphoro amidite can be introduced into a commercially-available ribonucleic acid in an organic solvent such as acetonitrile or dichloromethane, using 2-cyanoethyl N,N,N',N'-tetraisopropylphosphorodiamidite, diisopropylamine and 1H-tetrazole.

Each of hydroxyl groups of the ribonucleic acid derivative is protected with protecting group $R_3$ which is similar to the protecting group $R_1$ as described above and an amino group of the nucleic acid base thereof is protected with an acyle group or a silyl group.

Examples of the nucleic acid bases used herein include purine bases such as adenine and guanine, and pyrimidine bases such as cytosine, uracil and thymine.

The condensation reaction between the compound (4) and the compound (5) is performed in an organic solvent such as acetonitrile, dichloromethane, tetrahydrofuran, diethylether, benzene, or dimethylformamide, more preferably, in a polar organic solvent, at low temperature, preferably in the temperature range of $-40°$ to $25°$ C., in the presence of an acid catalyst. For example, an acid catalyst is added to the reaction mixture while maintaining at low temperature. Thereafter, the reaction is allowed to proceed while gradually increasing the temperature. As the acid catalysts, an organic acid is preferably used. The organic acid includes 1H-tatrazole, DL camphor-sulfonic acid, pyridium-p-toluene sulfonate, p-toluenesulfonyl acid (tosyl acid) and the like.

More specifically, the condensation reaction between the compound (4) and the compound (5), is started by adding 1H-tetrazole to a mixture of the compound (4) and the compound (5) in the aforementioned organic solvent at $-40°$ C. and is performed while gradually increasing the temperature to room temperature.

Subsequently, the phosphate portion of the phosphite derivative (6) obtained in the aforementioned condensation reaction is oxidized to obtain a phosphate derivative (9). The oxidation is performed in an organic solvent such as acetonitrile, benzene or dimethylformamide at e.g., $0°$ to $25°$ C. in the presence of an oxidizing agent of the same as or a larger amount than that of the phosphite derivative. As the oxidizing agents, t-butylhydroperoxide or iodine/pyridine could be used.

Removal of a protective group from phosphate derivative (9) is performed by an alkali treatment. Examples of alkalis used herein include ammonia water, sodium carbonate, sodium methoxide, sodium ethoxide, 1,8-diazabicyclo[5,4,0]-7-undecene (DBU), 1,8-diazabicyclo[5,4,0]-7-nonene (DBN), triethylamine, and diisopropylamine.

More specifically, the alkali treatment is performed in one step reaction using ammonia water, sodium carbonate, sodium methoxide or sodium ethoxide in water-methanol at room temperature.

The following reactions represented by the following scheme can be performed to obtain the sialic acid derivative (1) from the phosphate derivative (9); a cyanoethyl group is removed from the phosphate derivative (9) by using tertiary amine E, thereby obtaining an intermediate (I), which is further deacetylated by an alkali treatment, thereby obtaining a sialic acid derivative (I).

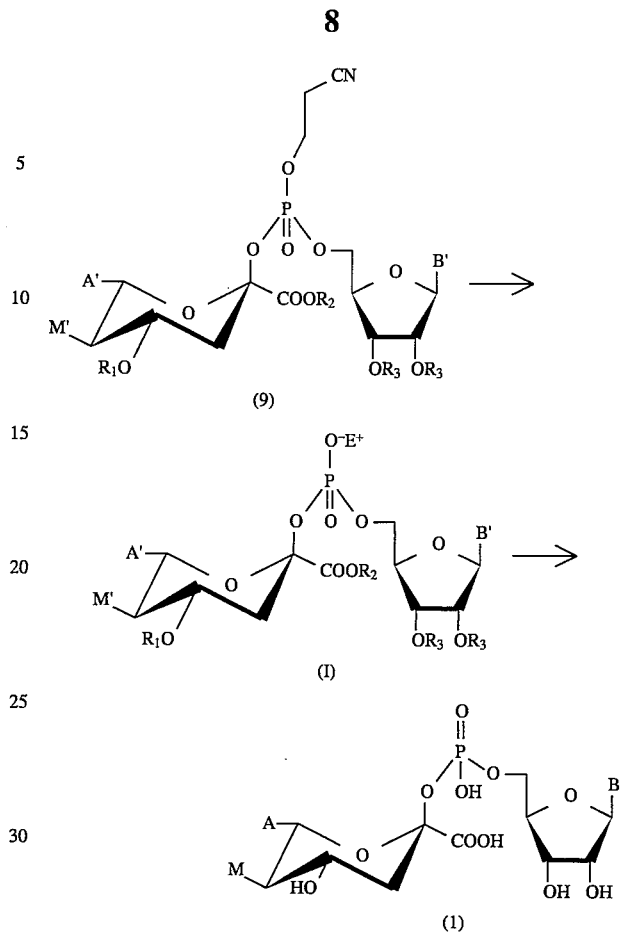

In these reactions, DBU, DBN, triethylamine and diisopropylamine may be used as tertiary amine E. As alkalis, ammonia water, sodium carbonate, sodium methoxide and sodium ethoxide can be used. A series of these reactions represented by the above scheme are performed at room temperature.

More specifically, the cyanoethyl group of the phosphate derivative (9) is removed using DBU/THF to obtain intermediate I. Intermediate I is deacetylated by treatment with a sodium methoxide to obtain the sialic acid derivative (1).

Since the compounds obtained in individual steps described above can be used in the following step without purification, this manufacturing method can be applied to a large-scale synthesis.

The novel sialic acid derivative (10) is a condensed compound of a sialic acid polymer and ribonucleic acid-5'-O-amidite and is a novel compound synthesized in accordance with the method of manufacturing the sialic acid derivative of the present invention. The sialic acid polymer has a binding activity to a sialic-acid binding substance such as a protein, namely hemaglutinine present on the surface layer of influenza virus. The binding activity of the sialic acid polymer is considered stronger than that of a sialic acid monomer. Likewise, the sialic acid polymer is contributory to realization of sialic acid's therapeutic application. The novel sialic acid derivative (10) of the present invention is useful to introduce a sialic acid polymer into a sugar chain.

BEST MODE OF CARRYING OUT THE INVENTION

Hereinbelow, Examples of the present invention will be described in detail.

EXAMPLE 1

Production of cytidine-5'-monophosphosialic acid (1a)

1.1 Synthesis of triacetylcytidine-5'-O-amidite (5a)

120 mg (331 µmol) of $N^4$-2',3'-acetylcytidine (Angew, Chem., 85(1), 43–44(1973)), 199 mg (662 µmol) of 2-cyanoethyl N,N,N', N'-tetraisopropylphosphoro amidite and 67 mg (662 µmol) of diisopropylamine were dissolved in 5.0 ml of anhydrous acetonitrile. To the solution obtained, 46 mg (662 µmol) of 1H-tetrazole was added at 0° C. After stirring at room temperature for 24 hours, the reaction solution was diluted with ethyl acetate. An organic layer obtained was washed with successive, a saturated aqueous sodium bicarbonate solution, and water. The washing-completed organic layer was dried over anhydrous magnesium sulfate and then concentrated. The residue obtained was dissolved in chloroform (5 ml), cooled to −78° C. and poured into 100 ml of pentane. A precipitate depositing in the previous step was filtrated to obtain a mixture (1:1)(186 mg, 65%) of diastereomers whose an asymmetric center is phosphorus atom of triacetylcytidine-5'-O-amidite (5a) represented by the following formula. The mixture was used in the following step without purification.

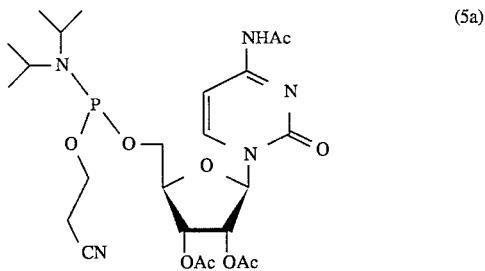

(5a)

wherein Ac represents an acetyl group. Hereinafter, Ac has the same definition.

Physical data of the obtained product are as follows $^1$H-NMR (CDCl$_3$) δ9.40 (bs, 1H, NH-4) 8.26, 8.24 (each d, each 0.5H, J=7.6 Hz, H-6) 7.44 (d, 1H, H-5) 6.37, 6.30 (each d, each 0.5H, J=4.9 Hz, H-1') 5.47–5.36 (m, 2H, H-2', 3') 2.76 (t, 1H, J=6.1 Hz, cyanoethyl CH$_2$) 2.25 (s, 3H, Ac) 2.11, 2.10, 2.07, 2.06 (each s, each 1.5H, each Ac) 1.28–1.24 (bs, 12H, Me)

$^{31}$P-NMR (CDCl$_3$) δ150.51, 149.67 ppm

1.2 Synthesis of Phosphite (6a)

40 mg (80.0 µmol) of tetra-O-acetylsialic acid (Chemische Berichte 1966, 99, 611–617))(4a) and 180 mg (300 µmol) of the compound (5a) synthesized in step 1.1 were subjected to an azeotropic distillation respectively twice using toluene. Each of the resultant solutions was evaporated to dryness. The residues of both solutions were combined and dissolved in 2 ml of anhydrous acetonitrile. The resultant reaction solution was cooled to −40° C. in argon gas flow. Subsequently, to the reaction solution, 21 mg (300 µmol) of 1H-tetrazole was added and stirred for 30 minutes. Thereafter, the temperature of the reaction solution was raised to room temperature. The reaction solution was diluted with ethyl acetate. The organic layer obtained was washed with a saturated sodium aqueous bicarbonate solution and water in consecutive order. After the organic layer was dried over anhydrous magnesium sulfate, the obtained residue was purified by silica gel column chromatography (hexane: acetone=1:2), thereby obtaining a diastereomer mixture (1.6:1) of phosphite represented by the following formula (6a) was obtained in a yield of 34 mg (44%). The diastereomer mixture obtained was used in the following step without purification.

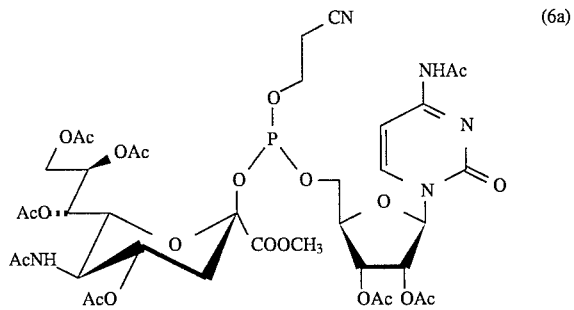

(6a)

Physical data of the obtained product are as follows:

$^1$H-NMR (CDCl$_3$) δ10.00 (S, 0.38, H, NH-4) 8.99 (s, 0.62H, NH-4) 8.07,(d, 0.38H, J=7.5 Hz, H-6) 7.81 (d, 0.62H, J=8.6 HZ, NH") 7.70 (d, 0.62H, J=7.5 HZ, H-6) 7.52 (d, 0.38H, H-5) 7.45 (d, 0.62H, J=7.5 HZ, H-5) 6.87 (d, 0.38H, J=10.0 HZ, NH") 6.11 (d, 0.38H, J=4.7 HZ, H-1') 5.18 (m, 0.62H, H-5") 3.87 (s, 1.14H, Me) 4.50 (dd, 0.62H, J=2.4, 12.1 Hz, H-9") 3.85 (s, 1.86H, Me) 2.70 (t, 1.24H, J=6.1 Hz, cyanoethyl CH2) 2.50 (dd, 0.38H, J=4.4, 12.9 Hz, H-3" eq) 2.48 (dd, 0.62H, J=4.9, 12.8 Hz, H-3" eq) 2.23, 2.19, 2.14, 2.13, 2.03, 1.97, 1.94, 1.85 (each s Ac)

$^{31}$P-NMR (CDCl$_3$) δ136.77, 134.28 ppm

1.3 Synthesis of phosphate (9a)

After 17 mg (17.6 µmol) of phosphite (6a) obtained in step 1.2 was dissolved in 1 ml of acetonitrile, 33 µl of t-butylhydroperoxide was added thereto at room temperature. 30 minutes thereafter, the reaction solution was diluted with ethyl acetate. The organic layer obtained was washed with a saturated sodium aqueous bicarbonate solution and water in consecutive order. The organic layer was dried over anhydrous magnesium sulfate and concentrated. The concentrate obtained was purified by a silica gel column chromatography (methanol:ethyl acetate=1:9), thereby obtaining phosphate (9a) (15 mg, 87%) represented by the following formula. The phosphate (9a) obtained was a mixture (1.6:1) of diastereomers whose an asymmetric center is a phosphorus atom.

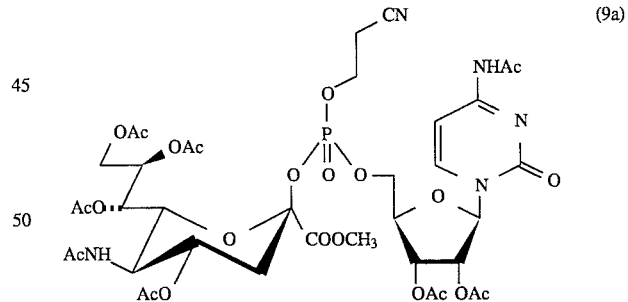

(9a)

Physical data of the obtained product are as follows:

$^1$H-NMR (CDCl$_3$) δ9.29 (bs, 0.38, H, NH) 9.22 (bs, 0.62H, NH) 7.69–7.56 (m, 2H, H-6×2, NH×2) 7.52 (d, 0.38H, J=7.5 Hz, H-5) 7.44 (d, 0.62H, J=7.4 Hz, H-5) 4.14 (dd, 0.62H, J=8.6, 12.0 Hz, H-9"a) 3.97 (dd, 0.38H, J=9.1, 12.2 Hz, H-9"a) 2.99 (dd, 0.38H, J=4.9, 13.7 Hz, H-3"e) 2.82 (t, 2H, J=6.1 Hz, CH$_2$) 2.65 (dd, 0.62H, J=4.8, 13.3 Hz, H-3" eq) 2.26, 2.24, 2.19, 2.18, 2.14, 2.13, 2.12, 2.11, 2.04, 1.99, 1.97, 1.96, 1.93, 1.85 (s, Ac)

$^{31}$P-NMR (CDCl$_3$) δ-7.61, -8.44 ppm

1.4 Synthesis of cytidine-5'-monophosphosialic acid (1a)

33 mg (33.7 µmol) of phosphate (9a) obtained in step 1.3 of Example 1 was dissolved in 1.5 ml of dry methanol. To this solution, 91 mg (1.69 mmol) of powdery sodium methoxide was added and stirred for 90 minutes at room temperature. PH of the solution obtained was 12 or more. Subsequently, 5 ml of water was added to the resultant solution and the solution was stirred for further 90 minutes. Thereafter, the reaction solution was lyophilized without any treatments and purified by gel filtration column (Sephadex G-15, water, 4° C.). Subsequently, a fractions containing cytidine-5'-monophosphosialic acid (1a) were allowed to pass through an anion exchange resin (AG 1-X8, formic acid type) to adsorb cytidine-5'-monophosphosialic acid (1a). Afterward, water is supplied in the anion exchange resin to remove impurities such as inorganic salts. Compound (1a) was then eluted from the anion exchange resin with ammonium carbonate (water→1M) and the eluate was lyophilized to obtain compound (1a) in a yield of 16 mg (75%).

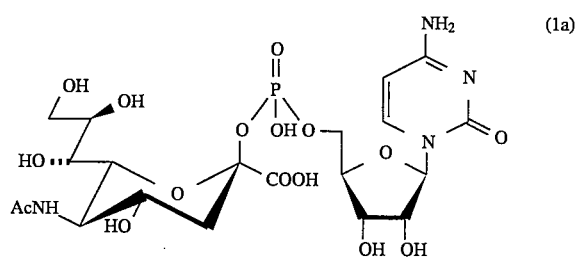
(1a)

Physical data of the obtained product are as follows:

$^1$H-NMR ($D_2O$, 300 MHz, HOD=4.81) δ7.97 (d, 1H, J=7.6 Hz, H-6) 6.12 (d, 1H, J=7.6 Hz, H-5) 5.98 (d, 1H, J=4.4 Hz, H-1') 4.06 (ddd, 1H, J=4.7, 10.9 Hz, H-4") 3.61 (dd, 1H, J=6.3, 11.7 Hz, H-9"a) 3.44 (d, 1H, J=9.4 Hz, H-7") 2.48 (dd, 1H, J=4.7, 13.1 Hz, H-3"eq) 2.04 (s, 3H, Ac) 1.64 (ddd, 1H, J=6.1, 13.1 Hz, H-3" ax)

$^{31}$P-NMR ($D_2O$, $H_3PO_4$=0.00 ppm) δ-4.43 ppm

EXAMPLE 2

73 mg (75 μmol) of the phosphate (9a) obtained in step 1.3 of Example 1 was dissolved in 1.0 ml of tetrahydrofuran. To this solution, 13.6 mg (90 μmol) of 1,8-diazabicyclo[5,4,0]-7-undecene (DBU) was added. After the solution was allowed to stand still at room temperature for 5 minutes, 40 mg (746 μmol) of sodium methoxide and 0.7 to 0.1 ml of methanol-water were added thereto. After allowed to stand still at room temperature for 12 hours, the solution was lyophlized. The residue was purified by gel filtration column (Sephadex G-15, 4° C., water) to obtain CMP-sialic acid (33 mg, 69%).

The physical data of the obtained product are coincide with those of Example 1 of step 1.4.

EXAMPLE 4

Synthesis of cytidine-5'-monophosphodisialic acid dimer (1b)

4.1 Synthesis of hexa-O-sialic acid dimer (4b)

50 mg (21 μmol) of 2-thiophenylsialic acid dimer (13) obtained by introducing a protecting group into N-actylneuraminic acid dimer (α, 2→)(made by Nacalai Tesque; trade name) was dissolved in 0.5 ml of acetone-water (20:1). To this solution, 9.5 mg (53 μmol) of N-bromosuccinimide was added. After stirred at room temperature for 30 minutes, the reaction solution was diluted with ethyl acetate and washed with a saturated sodium aqueous bicarbonate solution. After an organic layer was separated, it was dried over anhydrous magnesium sulfate and concentrated. The obtained residue was purified by silica gel column chromatography (methanol:ethyl acetate=1:19) to obtain hexa-O-silaic acid dimer (4b) (16 mg, 89%).

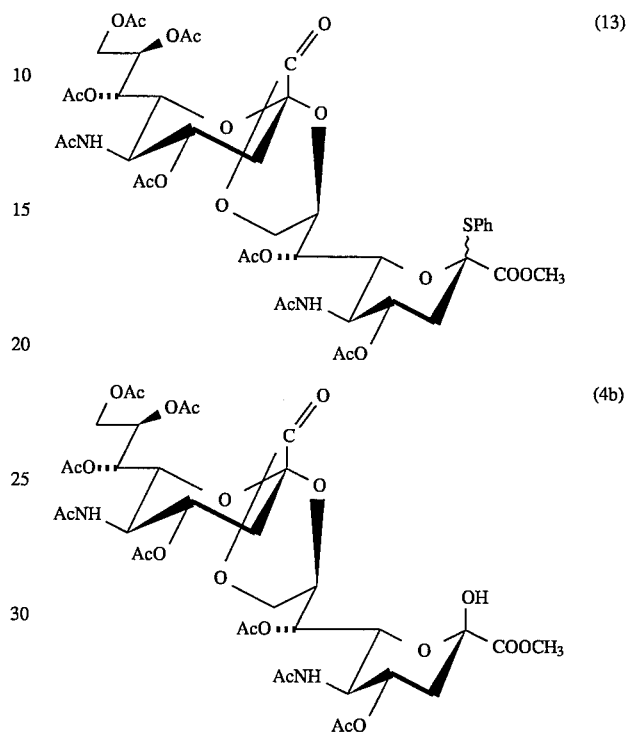

Physical data of the obtained product are as follows:

$^1$H-NMR ($CDCl_3$) δ5.76 (d, 1H, J=10.4 Hz, NH) 5.43 (d, 1H, J=10.4 Hz, NH) 3.89 (s, 3H, 0 Me) 2.45 (dd, 1H, J=5.6, 13.3 Hz, H-3' eq) 2.34–2.25 (m, 2H, H-3 ax, 3 eq) 2.18, 2.15, 2.08, 2.05, 1.94, 190 (each s, each 3H, Ac) 2.04 (s, 6H, AC, ×2)

4.2 Synthesis of Phosphite (6b)

21 mg (24.7 μmol) of hexa-O-sialic acid dimer (4b) synthesized in step 4.1 and 97 mg (173 μmol) of triacetyl-cytidine-5'-O-amidite (5a) synthesized in step 1.1 of Example 1 was respectively subjected to an azeotropic distillation twice using dry toluene. Each of the above-obtained solutions was evaporated to dryness. The residues of both solutions were combined and dissolved in 1.4 ml of anhydrous acetonitrile. This solution was cooled to −40° C. in argon gas flow. Subsequently, to this solution, 12 mg (173 μmol) of 1H-tetrazole was added. After stirred for 30 minutes, the temperature was raised to room temperature. The reaction solution was diluted with ethyl acetate and the organic layer obtained was washed with a saturated sodium aqueous bicarbonate solution and water in consecutive order. After the organic layer was dried over anhydrous magnesium sulfate, the residue obtained was purified by silica gel column chromatography hexane:acetone=1:3) to obtain diastereomer mixture (2:1) of a phosphite (6b) represented by the following formula in a yield of 15 mg (47%). Diastereomer mixture obtained was used in the following step without purification.

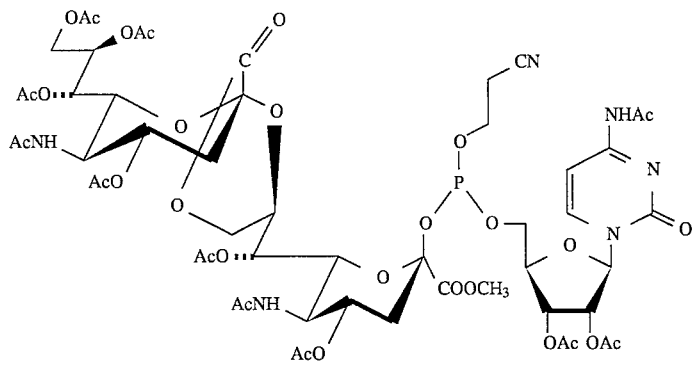

(6b)

Physical data of the obtained product are as follows:
$^1$H-NMR (CDCl$_3$) δ9.30 (bs 1H, NH) 7.80 (d, 1H, J=9.0 Hz, NH) 7.52, 7.45 (each d, each 1H, J=7.4 Hz, H-6, -5) 6.16 (bs, 1H, H-1') 5.95 (dd, 1H, J=3.6, 6.6 Hz, H-2") 5.62 (t, 1H, J=6.6 Hz, H-3') 3.89 (s, 3H, Me) 2.69 (t, 2H, J=6.3 Hz, CH$_2$) 2.51 (dd, 1H, J=4.8, 13.0 Hz, H-3''' eq) 2.32, 2.25, 2.14, 2.12, 2.09, 2.05, 2.04, 1.98, 1.88 (each s, each 3H, Ac)
$^{31}$P-NMR (CDCl$_3$) δ135.30, 133.52 ppm 4.3 Synthesis of Phosphate (9b)

1.6 mg (1.2 μmol) of the phosphite (6b) obtained in step 4.2 was dissolved in 0.1 ml of acetonitrile. To this solution, 20 μl of t-butylhydroperoxide was added at room temperature. 10 minutes later, the reaction solution was diluted with ethyl acetate. The organic layer obtained was washed with a saturated sodium aqueous bicarbonate solution and water in consecutive order. The organic layer was dried over anhydrous magnesium sulfate and concentrated. The concentrated obtained was purified by silica gel column chromatography (methanol:ethyl acetate=1:9) to obtain a phosphate (9b) represented by the following formula in a yield of 1.5 mg (94%). The phosphate (9b) obtained was a mixture of diastereomers whose an asymmetric center is a phosphor atom.

H-1') 5.94 (dd, 1H, J=2.5, 6.6 Hz, H-2') 5.76 (t, 1H, J=6.6 Hz, H-3') 3.92 (s, 3H, Me) 2.80 (t, 21H, J=6.1 Hz, CH$_2$) 2.60 (dd, 1H, J=6.5, 14.8 Hz, H-3''' eq) 2.33, 2.26, 2.15, 2.14, 2.09, 2.04, 2.03, 2.00, 1.88 (each s, each 3H, Ac) 2.05 (s, 6H, Ac) 1.41 (dd, 1H, J=11.5, 13.8 Hz, H-3" ax)
$^{31}$P-NMR (CDCl$_3$) δ6.86 ppm 4.4 Synthesis of cytidine-5'-monophosphodisialic acid dimer (1b)

22 mg (17 μmol) of the phosphate (9b) obtained in step 4.3 of Example 4 was dissolved in 0.4 ml of tetrahydrofuran. To this solution, 3 mg (20 μmol) of 1,8-diazabicyclo[5,4,0]-7-undecene (DBU) was added. After the solution was allowed to stand still at room temperature for 5 minutes, 22 mg (407 μmol) of sodium methoxide and 0.2 ml to 0.4 ml of methanol-water were added thereto. After allowed to stand still at room temperature for 12 hours, the solution was lyophlized. The residue was purified by gel filtration column (Sephadex G-15, 4° C., 1 mM NH$_4$OH) to obtain CMP-sialic acid dimer (9 mg, 56%).

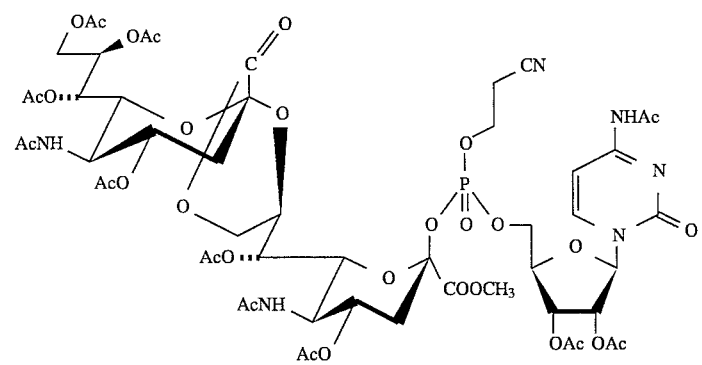

(9b)

Physical data of the obtained product are as follows:
$^1$H-NMR (CDCl$_3$) δ9.97 (bs, 1H, NH) 7.72 (d, 1H, J=9.3 Hz, NH") 7.48, 7.44 (each d, 1H, J=7.4 Hz, H-6, -5) 6.29 (bs, 1H,

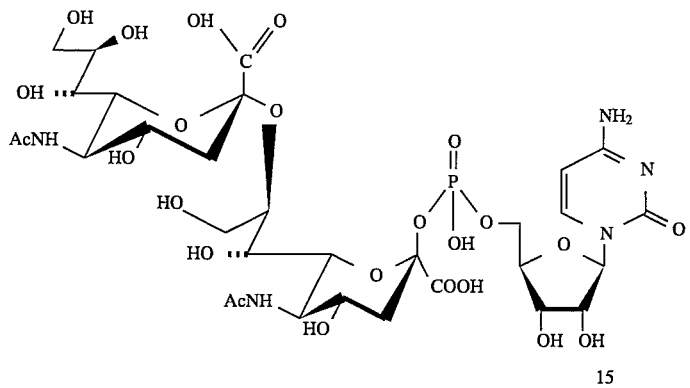

Physical data of the obtained product are as follows:

$^1$H-NMR ($D_2O$, 500 MHz, 50 mM $NH_4HCO_3$, HOD= 4.80) δ7.86 (d, 1H, J=7.5 Hz, H-6) 6.01 (d, 1H, J=7.5 Hz, H-5) 5.88 (d, 1H, J=2.9 Hz, H-1') 2.64 (dd, 1H, J=4.3, 12.6 Hz, H-3''' eq) 2.44 (dd, 1H, J=4.7, 13.3 Hz, H-3'' eq) 1.98, 1.92 (each s, each 3H, Ac) 1.64 (dd, 1H, J=12.1, 12.6 Hz, H-3''' ax) 1.59 (ddd, 1H, J=2.7, 13.3 Hz, H-3'' ax)

$^{31}$P-NMR ($D_2O$, $H_3PO_4$=0.00 ppm) δ-5.48 ppm

According to the method of manufacturing a sialic acid derivative of the present invention, a CMP-sialic acid analogue useful as a sialic acid donor to be bonded to non-reducing terminal of a sugar chain which mediates intercellular interaction in a living body can be obtained by using an inexpensive reagents, and simultaneously a sialic acid derivative can be obtained in a high degree of purity. As a result, industrial large-scale production of the sialic acid derivative can be attained.

Furthermore, a novel sialic acid derivative of the present invention is useful to introduce a sialic acid polymer into a sugar chain and new therapeutic methods can be realized using the novel sialic acid derivative.

We claim:

1. A method of manufacturing a sialic acid derivative (1) represented by the following formula:

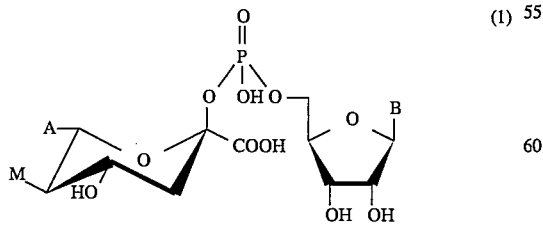

wherein

M is a hydroxyl group or an acetamide group, and A is a group represented by the following formula (3):

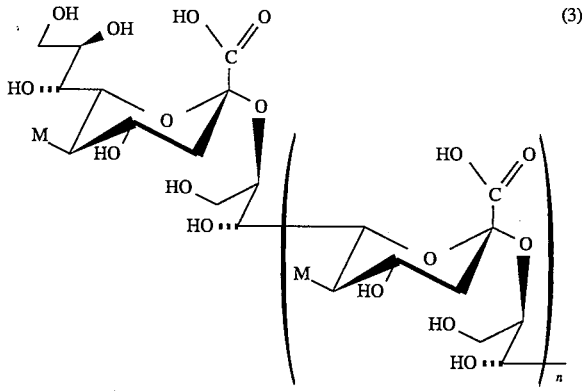

wherein n is an integer of 0–3, M is the same as defined above, and B is a substituted or unsubstituted nucleic acid base, comprising:

(a) performing a condensation between a compound (4) and a compound (5) represented by the following formulas, in the presence of an acid catalyst, thereby obtaining a phosphite derivative (6) represented by the following formula,

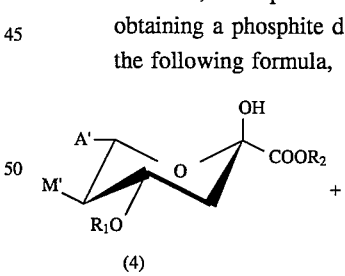

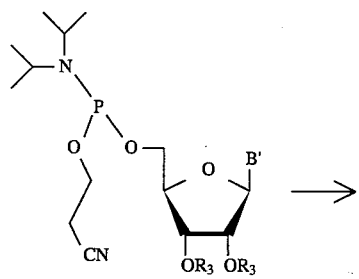

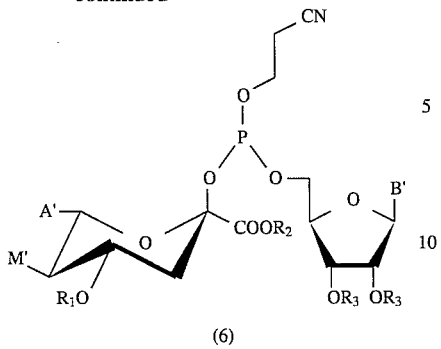

(6)

wherein M' indicates —$OR_1$ or an acetamide group,
$R_1$ and $R_3$ are an acyl group or a silyl group and may be the same or different from each other,
$R_2$ is an alkyl group, and
A' indicates a group represented by the following formula (8):

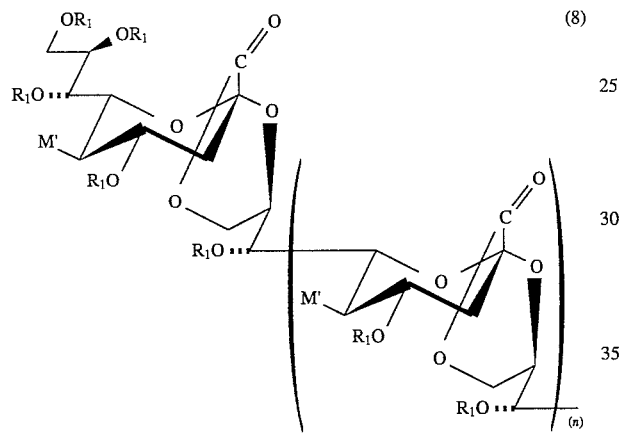

(8)

wherein n is an integer of 0–3, $R_1$ and M' are the same as defined above,
and B' is a nucleic acid base whose exocyclic amino group is protected by an acyl group or a silyl group;

(b) oxidizing said phosphite derivative (6) with an oxidizing agent, thereby obtaining a phosphate derivative (9) represented by a formula (9) shown below,

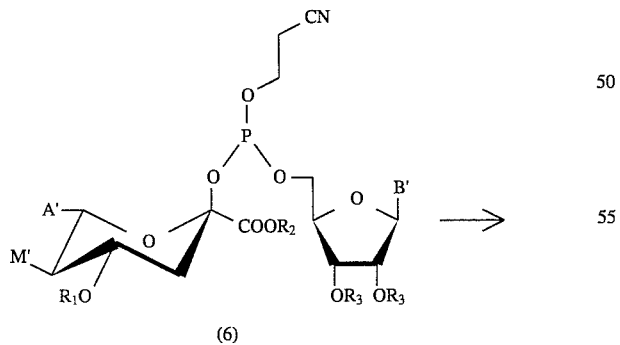

(6)

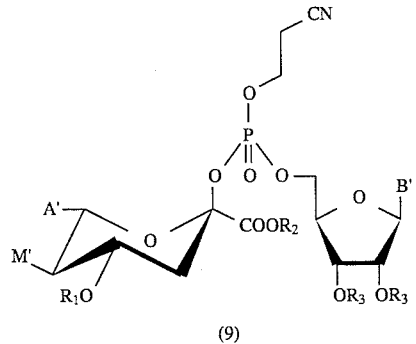

(9)

wherein M', A', B' and $R_1$ to $R_3$ are the same as defined above; and (c) deprotecting said phosphate derivative (9) with an alkali, thereby obtaining a sialic acid derivative (1),

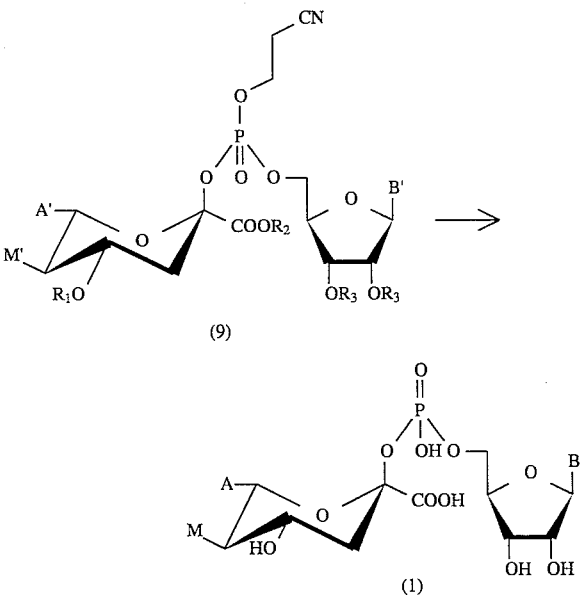

wherein M', M, A, A', B, B' and $R_1$ to $R_3$ are the same as defined above.

2. A method of manufacturing a sialic acid derivative (1) represented by the following formula:

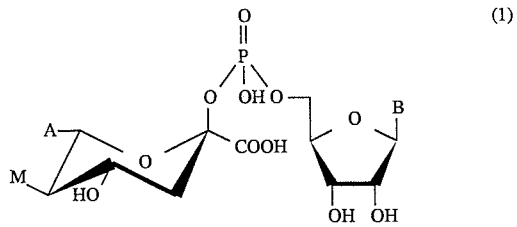

(1)

wherein

M is a hydroxyl group or an acetamide group, and A is a group represented by the following formula (3):

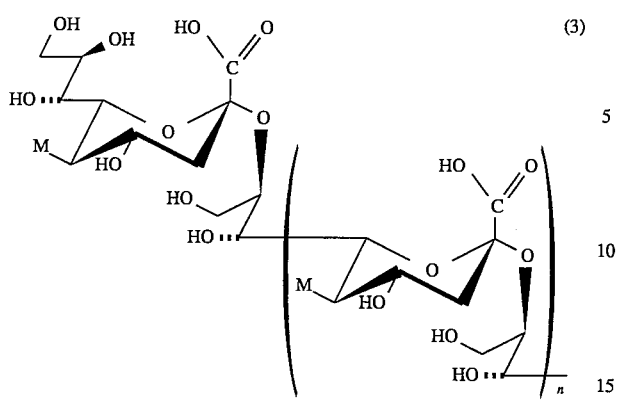

(3)

wherein n is an integer of 0–3, M is the same as defined above, and B is a substituted or unsubstituted nucleic acid base, comprising:

(a) performing a condensation between a compound (4) and a compound (5) represented by the following formulas, in the presence of an acid catalyst, thereby obtaining a phosphite derivative (6) represented by the following formula,

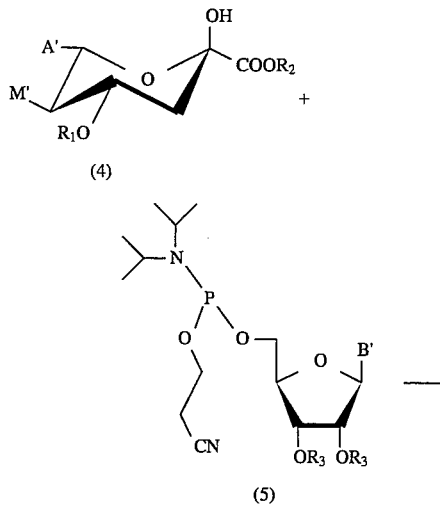

wherein M' indicates —$OR_1$ or an acetamide group, $R_1$ and $R_3$ are an acyl group or a silyl group and may be the same or different from each other, $R_2$ is an alkyl group, and A' indicates a group represented by the following formula (8):

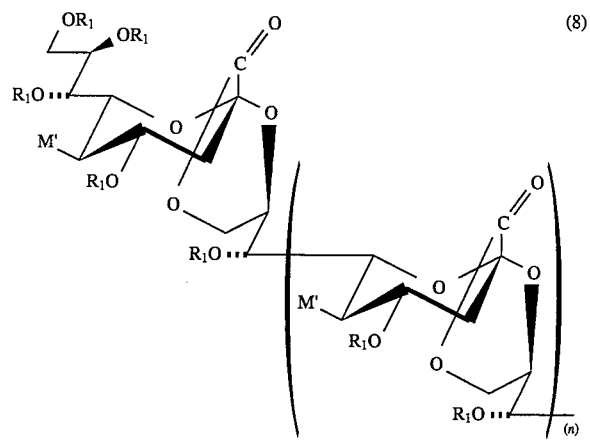

wherein n is an integer of 0–3, $R_1$ and M' are the same as defined above, and B' is a nucleic acid base whose exocyclic amino group is protected by an acyl group or a silyl group;

(b) oxidizing said phosphite derivative (6) with an oxidizing agent, whereby obtaining a phosphate derivative (9) represented by the following formula,

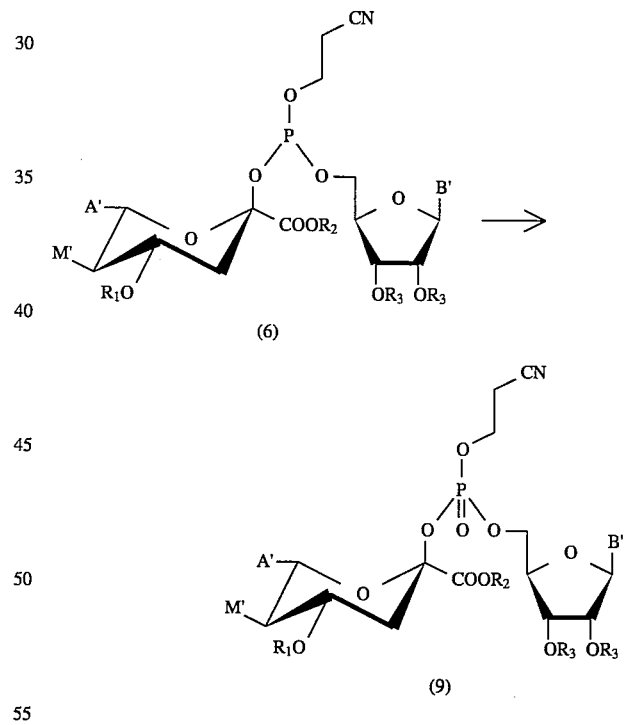

wherein M', A', B' and $R_1$ to $R_3$ are the same as defined above;

(c) deprotecting a cyanoethyl group of said phosphate derivative (9) with a tertiary amine, thereby obtaining an intermediate (I),

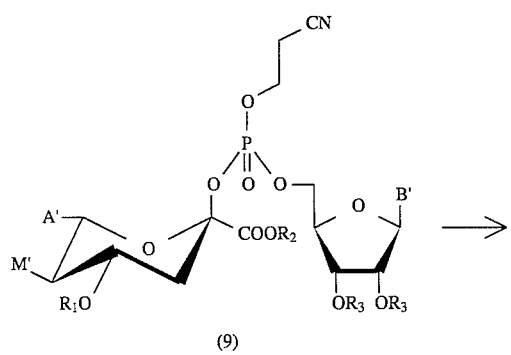

(9)

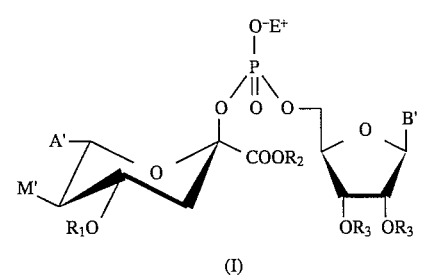

(I)

wherein E represents a tertiary amine, M', A' and $R_1$ to $R_3$ are the same as defined above; and (d) deacetylating said intermediate (I) with an alkali, thereby obtaining a sialic acid derivative (1),

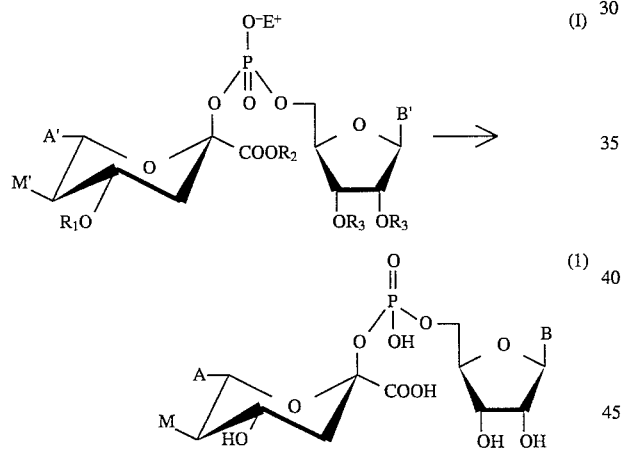

wherein M', M, A, A', B, B', E, $R_1$ to $R_3$ are the same as defined above.

3. A sialic acid derivative (10) represented by the following formula:

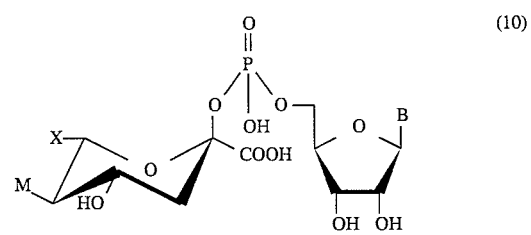

wherein

M is a hydroxyl group or an acetamide group, and X is a group represented by the following formula (11):

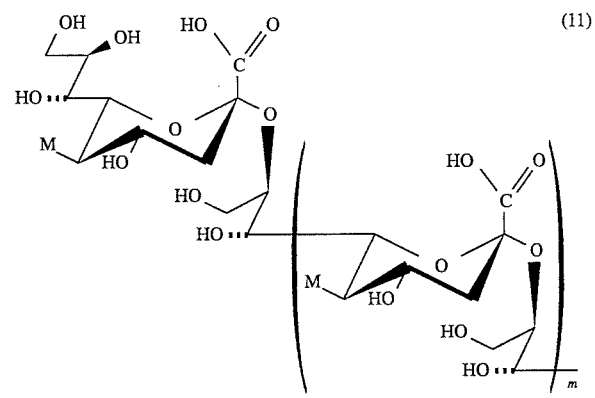

wherein m is an integer of 0 to 3, M is the same as defined above, and B is a substituted or unsubstituted nucleic acid base.

* * * * *